(12) United States Patent
Lien et al.

(10) Patent No.: US 9,125,557 B2
(45) Date of Patent: Sep. 8, 2015

(54) MAGNETIC MANEUVERING SYSTEM FOR CAPSULE ENDOSCOPE

(75) Inventors: Gi-Shih Lien, Taipei (TW); Chih-Wen Liu, Taipei (TW); Joe-Air Jiang, Taipei (TW); Cheng-Long Chuang, Taipei (TW); Ming-Tsung Teng, Taipei (TW)

(73) Assignee: Gi-Shih Lien, Taipei (TW)

( * ) Notice: Subject to any disclaimer, the term of this patent is extended or adjusted under 35 U.S.C. 154(b) by 203 days.

(21) Appl. No.: 13/483,119

(22) Filed: May 30, 2012

(65) Prior Publication Data

US 2013/0231530 A1    Sep. 5, 2013

(30) Foreign Application Priority Data

Mar. 5, 2012   (TW) .............................. 101107285 A

(51) Int. Cl.
| | | |
|---|---|---|
| A61B 1/00 | (2006.01) |
| A61B 1/04 | (2006.01) |
| A61B 1/06 | (2006.01) |
| A61B 5/00 | (2006.01) |
| A61B 5/07 | (2006.01) |

(52) U.S. Cl.
CPC ............. *A61B 1/00158* (2013.01); *A61B 1/041* (2013.01)

(58) Field of Classification Search
USPC ......... 600/101, 109–114, 160–182, 407, 476, 600/300–302, 424; 604/890.1; 128/899
See application file for complete search history.

(56) References Cited

U.S. PATENT DOCUMENTS

| | | | | |
|---|---|---|---|---|
| 5,681,260 | A * | 10/1997 | Ueda et al. ..................... | 600/114 |
| 2007/0221233 | A1 * | 9/2007 | Kawano et al. ................ | 128/899 |
| 2009/0012363 | A1 * | 1/2009 | Liu et al. ........................ | 600/127 |

* cited by examiner

*Primary Examiner* — Ryan Henderson
(74) *Attorney, Agent, or Firm* — Amin, Turocy & Watson, LLP

(57) ABSTRACT

A magnetic maneuvering system for capsule endoscope includes the capsule endoscope, an annular fitting sleeved around the outer surface of the capsule endoscope. A plurality of magnetic driven parts are provided and distributed on the annular fitting member. The control device includes a magnetic driving part for magnetically actuating the magnetic driven parts, thus enabling the capsule endoscope to rotate and move in an organism as a result of the actuation of the magnetic driven parts. By magnetically controlling the magnetic driven parts, the capsule endoscope is allowed to rotate or move under the control of the control device to achieve better image retrieval results and improve over the poor image retrieval results obtained by the prior art since the location and direction of a traditional capsule endoscope, relying solely on the contractions of the digestive tract, cannot be controlled.

9 Claims, 3 Drawing Sheets

MAGNETIC MANEUVERING SYSTEM FOR CAPSULE ENDOSCOPE

FIELD OF THE INVENTION

The present invention relates to systems for controlling a capsule endoscope, and, more particularly, to a magnetic maneuvering system for controlling the location and the direction of a capsule endoscope.

BACKGROUND OF THE INVENTION

In the diagnosis and treatment of the interiors of organisms, an endoscope is an effective and commonly used tool. An endoscope is traditionally equipped with a camera lens at the front end of its fiber-optic catheter. The camera lens and the fiber-optic catheter are inserted into the organism through a patient's mouth or anus, and images of the internal of the organism are captured by the camera lens and are sent back through the fiber-optic catheter to an external machine.

However, since the digestive system of the human body is quite long and has many bent segments, the photographic results of the camera are thus affected. Therefore, sending the fiber-optic catheter into the digestive system of the human body by swallowing is not a very comfortable experience.

In recent years, capsule endoscopy has been developed in the field of medical equipment. Due to its small size, the capsule endoscope can be swallowed more easily by the patient, and, without the fiber-optic catheter, the length of the digestive system is not a concern. Moreover, the movement of the capsule endoscope inside the digestive system relies on the contractions of the digestive tract, so it has a better photographic result compared to the traditional intubational endoscope.

However, since the capsule endoscope is to be swallowed into the digestive system, its size cannot be too large, but a small capsule endoscopy tend to welter in the organs such as the stomach or the large intestine, so images of the digestive system cannot be effectively obtained. Furthermore, since the existing capsule endoscope is solely moved through the digestive system by the contractions of the digestive tract, thus the direction and location of the capsule endoscope cannot be controlled from outside the organism.

Recently, instrument such as a nuclear magnetic resonance (NMR) instrument has been employed to guide, move or rotate the shooting angle of the capsule endoscope inside the organism by producing a huge magnetic field outside the organism, thereby obtaining a better photographic result. However, such external instrument cannot be easily acquired, and the cost of acquisition is high. Moreover, the handling of it is not simple and intuitive for the operators.

Therefore, there is a need to overcome the abovementioned shortcomings of the prior art.

SUMMARY OF THE INVENTION

An objective of the present invention is to provide a magnetic maneuvering system for a capsule endoscope, which is capable of controlling the location and the shooting angle of the capsule endoscope by controlling magnetic driven parts of the capsule endoscope with a magnetic driving part of a control device through magnetism.

A magnetic maneuvering system for a capsule endoscope provided by the present invention includes: the capsule endoscope, an annular fitting member and a control device. The capsule endoscope is for use in retrieving images of an interior of an organism. The annular fitting member is sleeved around the outer surface of the capsule endoscope and has a plurality of magnetic driven parts provided thereon. The control device includes a magnetic driving part for controlling the capsule endoscope inside the organism from outside, wherein the control device actuates the plurality of magnetic driven parts by the magnetic driving part via magnetism, for enabling the capsule endoscope to rotate and move in the organism corresponding to the actuation of the magnetic driven parts.

From the above, it can be seen that the magnetic driving part of the control device of the present invention magnetically controls the magnetic driven parts of the capsule endoscope, so the capsule endoscope rotates or moves in the organism under the control of the control device, thereby fully retrieving the images of the interior of the organism and addressing the prior-art problem that the direction and location of the capsule endoscope inside the organism cannot be controlled. The present invention further provides a cheaper solution compared to the conventional NMR technique.

BRIEF DESCRIPTION OF THE DRAWINGS

The present invention can be more fully understood by reading the following detailed description of the preferred embodiments, with reference made to the accompanying drawings, wherein.

DETAILED DESCRIPTION OF THE EMBODIMENTS

The present invention is described by the following specific embodiments. Those with ordinary skills in the arts can readily understand the other advantages and functions of the present invention after reading the disclosure of this specification. The present invention can also be implemented with different embodiments. Various details described in this specification can be modified based on different viewpoints and applications without departing from the scope of the present invention.

Figure 1:
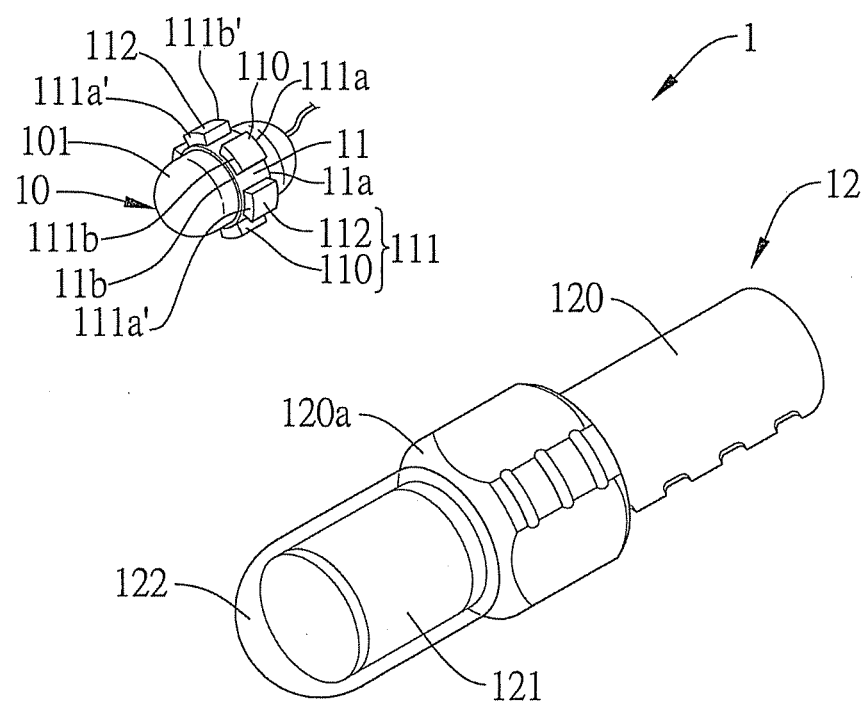
FIG. 1 is a schematic diagram depicting a magnetic maneuvering system for a capsule endoscope according to the present invention.

Referring to FIG. 1, a schematic diagram depicting a magnetic maneuvering system for a capsule endoscope 1 according to the present invention is shown. As shown, the magnetic maneuvering system for a capsule endoscope 1 includes a capsule endoscope 10, an annular fitting member 11, and a control device 12. The capsule endoscope 10 has an outer surface 101. The annular fitting member 11 is sleeved around the outer surface 101 of the capsule endoscope 10; the annular fitting member 11 has a first end 11a and a second end 11b opposite to the first end 11a, and a plurality of magnetic driven parts 111 comprising first magnetic driven parts 110 and second magnetic driven parts 112 are provided on the surface of the annular fitting member 11. The control device 12 includes a rod 120, a magnetic driving part 121, and a cover 122. The rod 120 has a top portion 120a. The magnetic driving part 121 and the cover 122 are provided at the top portion 120a of the rod 120 and the cover 122 encases the magnetic driving part 121.

The magnetic maneuvering system for a capsule endoscope 1 according to the present invention allows the magnetic driving part 121 of the control device 12 to drive the magnetic driven parts 111 through magnetism, so that the capsule endoscope 10 can be rotated or moved along with the magnetic driven parts 111 under the control of the magnetic driving part 121. The magnetic driving part 121 can be a permanent magnet or electromagnetic coil.

Figure 2:
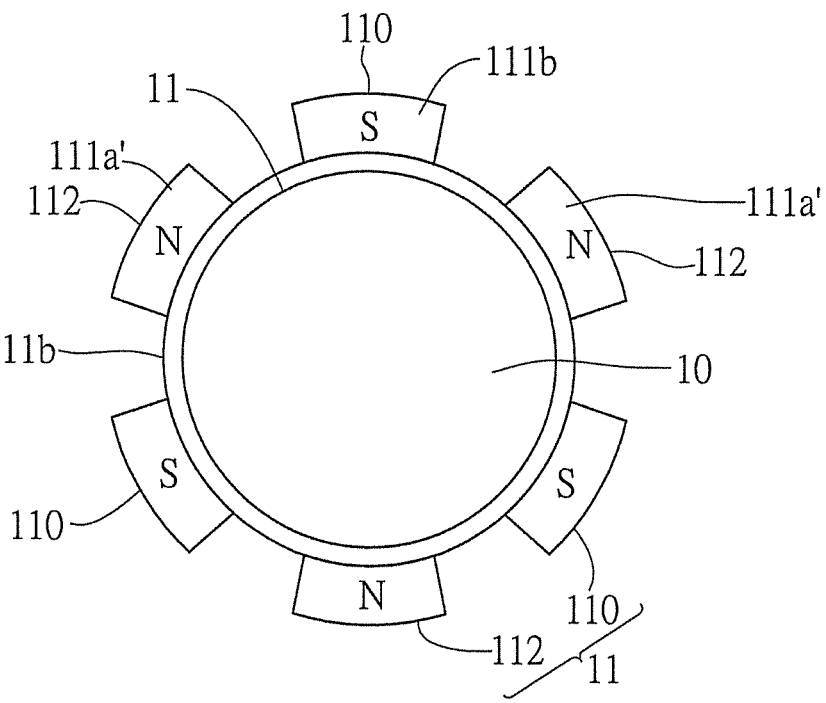
FIG. 2 is a schematic diagram depicting an arrangement of magnets for the magnetic driven parts of the annular fitting part shown in FIG. 1.

Referring to FIG. 2, a schematic diagram depicting an arrangement of magnets for the magnetic driven parts of the annular fitting part is shown. The plurality of magnetic driven parts 111 are provided and distributed on the surface of the annular fitting member 11. Each magnetic driven part 111 includes an N pole 111a, 111a' and an S pole 111b, 111b'; the N pole 111a of each of the first magnetic driven parts 110 is positioned in the first end 11a, and the S pole 111b of each of the first magnetic driven parts 110 is positioned in the second end 11b; the N pole 111a' of each of the second magnetic driven parts 112 is positioned in the second end 11b, and the S pole 111b' of each of the second magnetic driven parts 112 is positioned in the first end 11a. FIG. 2 is a top view of the capsule endoscope 10 shown in FIG. 1, so the various magnetic driven parts 111 shown in FIG. 2 are the tops of the magnetic driven parts 111. The magnetic driven parts 111 are arranged such that the poles of any two adjacent magnetic driven parts 111 are opposite to each other in the first end 11a or in the second end 11b. In other words, the first magnetic driven parts 110 and the second magnetic driven parts 112 interlace with each other. For example, if a first magnetic driven part 110 is arranged on the annular fitting member 11 with the S pole 111b facing upwards, then the facing upward poles of two adjacent second magnetic driven parts 112 positioned at either side of said first magnetic driven part 110 are N poles 111a', opposite to the S pole 111b.

In addition, in order for the annular fitting member 11 to rotate under the control of the control device 12, the plurality of magnetic driven parts 111 are provided and distributed on the annular fitting part 11. Although six magnetic driven parts 111 are shown to be distributed on the annular fitting member 11, this number is merely for illustration purpose, and the present invention is not limited to this, as long as there is a plurality of magnetic driven parts 111. Preferably, the number of magnetic driven parts 111 is even.

The ways in which the N poles 111a, 111a' and the S poles 111b, 111b' of the magnetic driven parts 111 are arranged, are similarly for illustration purpose only.

Figure 3:
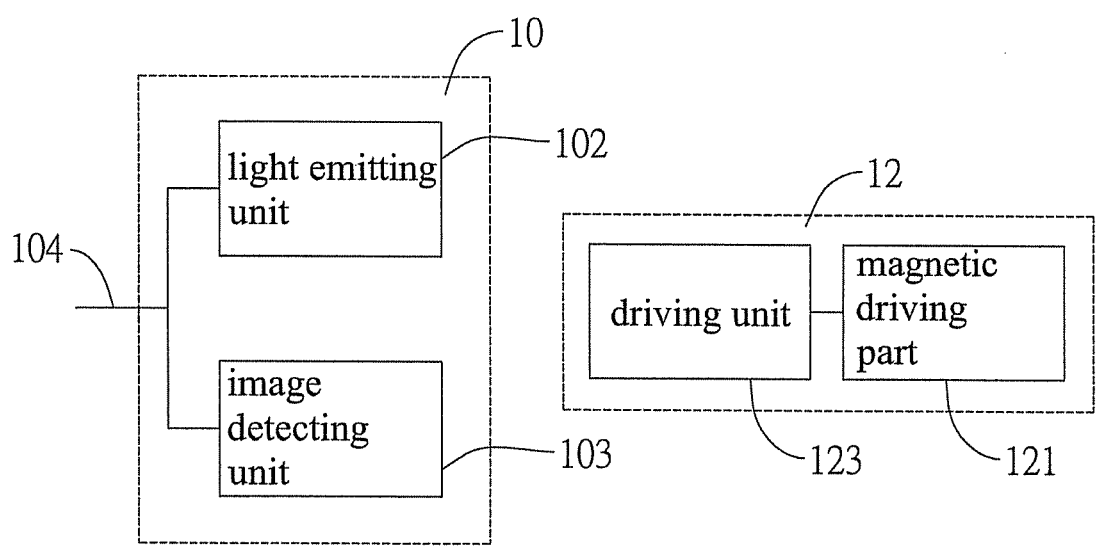
FIG. 3 is a circuit block diagram depicting the magnetic maneuvering system for a capsule endoscope according to the present invention.

Referring to FIG. 3, a circuit block diagram depicting the magnetic maneuvering system for a capsule endoscope according to the present invention is shown. The capsule endoscope 10 includes a light emitting unit 102, an image detecting unit 103, and a power and signal transmitting unit 104. The light emitting unit 102 is provided within the capsule endoscope 10 for providing a light source required by the capsule endoscope 10. The image detecting unit 103 is similarly provided within the capsule endoscope 10 for retrieving images of the interior of an organism. The power and signal transmitting unit 104 is electrically connected to light emitting unit 102 and image detecting unit 103 for supplying power to the light emitting unit 102, and transmitting the images retrieved by the image detecting unit 103 to the outside.

The control device 12 includes a driving unit 123 provided within the rod 120 of the control device 12. The driving unit 123 is electrically connected to the magnetic driving part 121 for driving the magnetic driving part 121. In an example of the present invention, a stepper motor and a power supply driving the stepper motor can be used as the driving unit 123 for rotating the magnetic driving part 121. Specifically, the stepper motor and the power supply are the conventional technology.

Although the power and signal transmitting unit 104 is shown as a transmission line in FIG. 3 for transmitting power to the capsule endoscope 10 and transmitting images to the outside, the transmission line is only one example of the present invention. In actual implementations, a wireless micro RF chip and a battery (not shown) can be used as the power and signal transmitting unit 104 in lieu of the transmission line for providing power and transmitting the captured images. However, using a transmission line as the power and signal transmitting unit 104 reduces the size of the capsule endoscope 10 as well as the cost of the capsule endoscope 10, so the transmission line is used as an example for illustrating the present invention, but the claims of the present invention are not limited thereto (that is, other implementations such as the wireless micro RF chip and the battery can also be employed).

Figure 4:
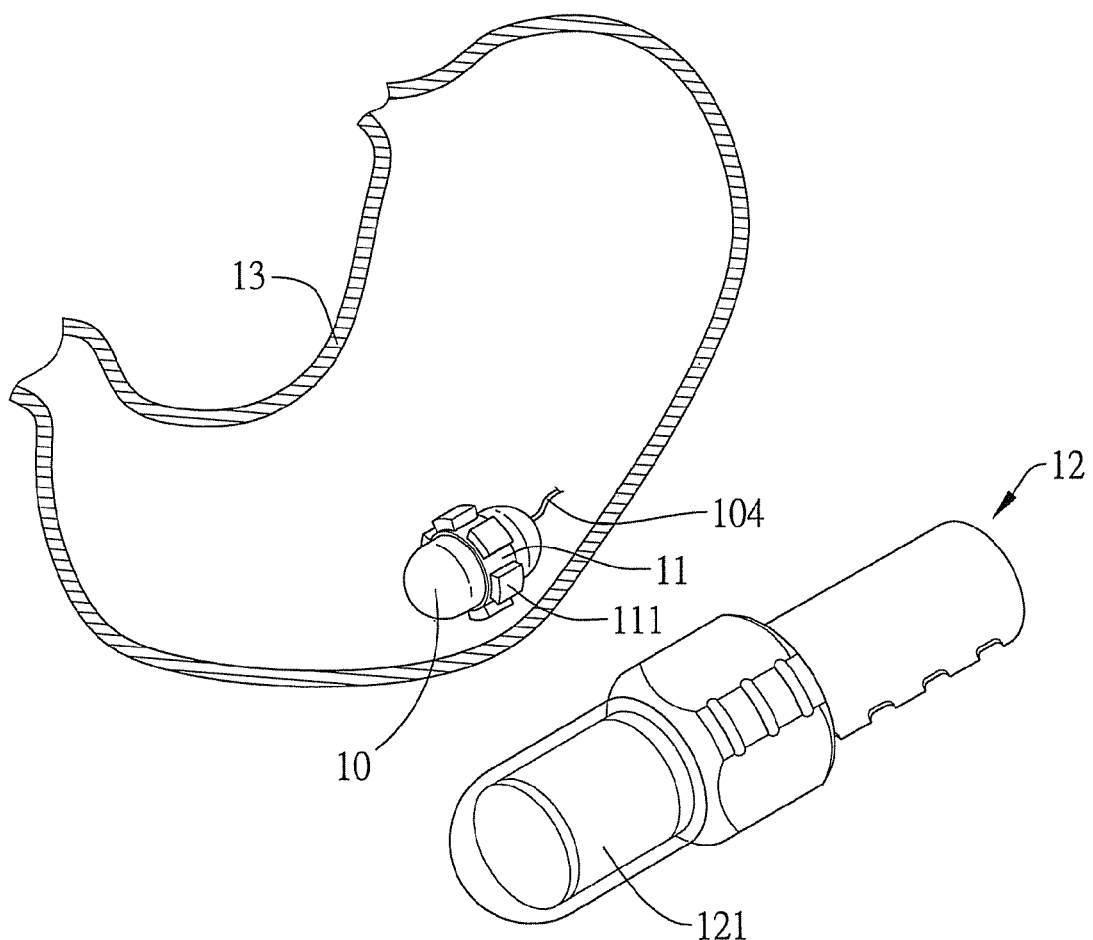
FIG. 4 is a schematic diagram illustrating a preferring embodiment according to the present invention.

Referring to FIG. 4, a schematic diagram illustrating a preferred embodiment according to the present invention is shown. In an actual implementation of the present invention, the capsule endoscope 10 is swallowed by an organism, so it enters into the interior 13 of the organism. Then, the power and signal transmitting unit 104 provides power to the capsule endoscope 10. Upon receiving the power, the light emitting unit 102 of the capsule endoscope 10 emits light to provide the light source necessary while the image detecting unit 103 is retrieving images. After images are retrieved by the image detecting unit 103, the images are transmitted to an external equipment for processing and/or displaying via the power and signal transmitting unit 104.

If a change in the location of the capsule endoscope 10 is desired, the control device 12 is moved close to where the capsule endoscope 10 is located, and as a result of this, the magnetic driven parts 111 of the annular fitting part 11 are attracted to the magnetic driving part 121 of the control device 12. By moving the control device 12, the capsule endoscope 10 will move correspondingly in the interior 13 of the organism due to the magnetism of the magnetic driving part 121. In addition, if a change in the shooting angle of the capsule endoscope 10 is desired, then the magnetic driven parts 111 of the annular fitting part 11 are first attracted to the magnetic driving part 121 of the control device 12. Thereafter, the magnetic driving part 121 is rotated by the driving unit 123 of the control device 12. This causes the magnetic driving part 121 of the magnetic driven parts 111 to rotate correspondingly due to the magnetism of the magnetic driving part 121. This allows the capsule endoscope 10 to spin along with the rotation of magnetic driven parts 111 in the interior 13 of the organism, thus changing the shooting angle of the capsule endoscope 10.

Alternatively, there is another method of changing the shooting angle of the capsule endoscope 10. First, the magnetic driven parts 111 of the annular fitting member 11 are attracted to the magnetic driving part 121 of the control device 12 similar to that described before, and then the magnetic driving part 121 are driven by the driving unit 123 to rotate three dimensionally, so that the capsule endoscope 10 also rotates three dimensionally with the magnetic driven parts 111 magnetically driven by the magnetic driving part 121 in the interior 13 of the organism, thereby changing the shooting angle of the capsule endoscope 10.

In an embodiment, a light emitting diode (LED) can be used as the light emitting unit 102 for providing the light source, and a CMOS camera is used as the image detecting unit 103 for capturing images of the interior 13 of the organism.

The above embodiments are only used to illustrate the principles of the present invention, and they should not be construed as to limit the present invention in any way. The above embodiments can be modified by those with ordinary skill in the art without departing from the scope of the present invention as defined in the following appended claims.

What is claimed is:

1. A magnetic maneuvering system, comprising:
    a capsule endoscope for use in retrieving images of an interior of an organism;
    an annular fitting member sleeved around an outer surface of the capsule endoscope and having a plurality of magnetic driven parts provided thereon, wherein the annular fitting member has a first end and a second end opposite to the first end, each of the plurality of magnetic driven parts includes an N pole and an S pole, the plurality of magnetic driven parts comprising first magnetic driven parts and second magnetic driven parts, wherein the N pole of each of the first magnetic driven parts is positioned in the first end, the S pole of each of the first magnetic driven parts is positioned in the second end, the N pole of each of the second magnetic driven parts is positioned in the second end, the S pole of each of the second magnetic driven parts is positioned in the first end, and any two adjacent ones of the magnetic driven parts are arranged in such a way that the poles thereof are opposite to each other in the first end of the annular fitting member; and
    a control device disposed exterior to the organism and including a magnetic driving part for controlling the capsule endoscope inside the organism, wherein the control device actuates the plurality of magnetic driven parts by the magnetic driving part via magnetism, for enabling the capsule endoscope to rotate and move in the organism corresponding to actuation of the magnetic driven parts.

2. The magnetic maneuvering system of claim 1, wherein the control device further includes a rod having a top, a driving unit provided in the rod, and a cover that covers the magnetic driving part, and wherein the magnetic driving part is provided on the top of the rod and coupled to the driving unit to be driven to rotate by the driving unit.

3. The magnetic maneuvering system of claim 2, wherein a stepper motor drives the magnetic driving part to perform a three-dimensional rotation.

4. The magnetic maneuvering system of claim 1, wherein the capsule endoscope includes a light emitting unit and an image detecting unit.

5. The magnetic maneuvering system of claim 4, wherein the light emitting unit is a light emitting diode.

6. The magnetic maneuvering system of claim 4, wherein the image detecting unit is a CMOS image detecting unit.

7. The magnetic maneuvering system of claim 1, wherein the capsule endoscope further includes a power and signal transmission unit.

8. The magnetic maneuvering system of claim 7, wherein the power and signal transmission unit is a transmission line.

9. The magnetic maneuvering system of claim 7, wherein the power and signal transmission unit includes a wireless micro RF chip and a battery.

\* \* \* \* \*